United States Patent
Materna et al.

(10) Patent No.: US 8,545,562 B1
(45) Date of Patent: Oct. 1, 2013

(54) DEPLOYABLE MEMBER FOR USE WITH AN INTERVERTEBRAL CAGE

(75) Inventors: Peter A. Materna, Metuchen, NJ (US);
James Bruffey, San Diego, CA (US);
Bret Hartzell, Massillon, OH (US);
Dale G. Davison, Copley, OH (US)

(73) Assignee: Theken Spine, LLC, Akron, OH (US)

( * ) Notice: Subject to any disclaimer, the term of this patent is extended or adjusted under 35 U.S.C. 154(b) by 376 days.

(21) Appl. No.: 12/752,032

(22) Filed: Mar. 31, 2010

Related U.S. Application Data

(63) Continuation-in-part of application No. 12/409,435, filed on Mar. 23, 2009, now abandoned, and a continuation-in-part of application No. 12/409,410, filed on Mar. 23, 2009, now abandoned, each which is a continuation-in-part of application No. 12/167,218, filed on Jul. 2, 2008, now Pat. No. 8,142,508, application No. 12/752,032, which is a continuation-in-part of application No. 12/368,898, filed on Feb. 10, 2009, now Pat. No. 8,292,958, which is a continuation-in-part of application No. 12/167,218, application No. 12/752,032, which is a continuation-in-part of application No. 12/368,895, filed on Feb. 10, 2009, now abandoned, and a continuation-in-part of application No. 12/368,893, filed on Feb. 10, 2009, now abandoned, and a continuation-in-part of application No. 12/368,890, filed on Feb. 10, 2009, now Pat. No. 8,366,774, and a continuation-in-part of application No. 12/368,888, filed on Feb. 10, 2009, now Pat. No. 8,100,972, each which is a continuation-in-part of application No. 12/167,218, application No. 12/752,032, which is a continuation-in-part of application No. 12/167,218.

(60) Provisional application No. 61/165,267, filed on Mar. 31, 2009, provisional application No. 61/037,551, filed on Mar. 18, 2008, provisional application No. 61/027,260, filed on Feb. 8, 2008, provisional application No. 60/947,557, filed on Jul. 2, 2007.

(51) Int. Cl.
*A61F 2/44* (2006.01)

(52) U.S. Cl.
USPC ..................................... 623/17.11

(58) Field of Classification Search
USPC ........................................ 623/17.11–17.16
See application file for complete search history.

(56) References Cited

U.S. PATENT DOCUMENTS

| | | |
|---|---|---|
| 1,503,124 A | 7/1924 | Hoppes |
| 1,824,739 A | 9/1931 | Johnson et al. |

(Continued)

FOREIGN PATENT DOCUMENTS

| | | |
|---|---|---|
| EP | 1104665 | 6/2001 |
| EP | 1338257 | 8/2003 |

(Continued)

*Primary Examiner* — Nicholas Woodall
(74) *Attorney, Agent, or Firm* — Middleton Reutlinger; Robert H. Eichenberger; Chad D. Bruggeman

(57) ABSTRACT

An implant may provide a body capable of being fit in an intervertebral space and a spin-plate rotatable with respect to the body. The spin-plate may a blade. The blade may possess grooves in its flat faces, or may be provided with an overhang. The path of the overhang or groove may be such that as the spin-plate advances in its rotation, a vertebra engaged with the blade is drawn toward the body of the implant. Pins may be placed in adjacent vertebrae such as to engage the spin-plate. Surgical methods are also described.

6 Claims, 6 Drawing Sheets

(56) References Cited

U.S. PATENT DOCUMENTS

| | | |
|---|---|---|
| 4,599,086 A | 7/1986 | Doty |
| 5,059,193 A | 10/1991 | Kuslich |
| 5,171,278 A | 12/1992 | Pisharodi |
| 5,306,309 A | 4/1994 | Wagner et al. |
| 5,336,223 A | 8/1994 | Rogers |
| 5,431,658 A | 7/1995 | Moskovich |
| 5,484,437 A | 1/1996 | Michelson |
| 5,593,409 A | 1/1997 | Michelson |
| 5,609,635 A | 3/1997 | Michelson |
| 5,653,762 A | 8/1997 | Pisharodi |
| 5,658,335 A | 8/1997 | Allen |
| 5,658,336 A | 8/1997 | Pisharodi |
| 5,665,122 A | 9/1997 | Kambin |
| 5,683,394 A | 11/1997 | Rinner |
| 5,683,464 A | 11/1997 | Wagner et al. |
| 5,702,455 A | 12/1997 | Saggar |
| 5,722,977 A | 3/1998 | Wilhelmy |
| 5,741,253 A | 4/1998 | Michelson |
| 5,749,916 A | 5/1998 | Richelsoph |
| 5,782,830 A | 7/1998 | Farris |
| 5,782,832 A | 7/1998 | Larsen et al. |
| 5,797,909 A | 8/1998 | Michelson |
| 5,800,547 A | 9/1998 | Schafer et al. |
| 5,861,041 A | 1/1999 | Tienboon |
| 5,865,845 A | 2/1999 | Thalgott |
| 5,885,299 A | 3/1999 | Winslow et al. |
| 5,888,227 A | 3/1999 | Cottle |
| 5,888,228 A | 3/1999 | Knothe et al. |
| 5,899,901 A | 5/1999 | Middleton |
| 5,944,658 A | 8/1999 | Koros et al. |
| 5,976,187 A | 11/1999 | Richelsoph |
| 5,980,522 A | 11/1999 | Koros et al. |
| 6,017,342 A | 1/2000 | Rinner |
| 6,030,390 A | 2/2000 | Mehdizadeh |
| 6,042,582 A | 3/2000 | Ray |
| 6,045,579 A | 4/2000 | Hochshuler et al. |
| 6,063,088 A | 5/2000 | Winslow |
| 6,066,175 A | 5/2000 | Henderson et al. |
| 6,080,155 A | 6/2000 | Michelson |
| 6,080,193 A | 6/2000 | Hochshuler et al. |
| 6,083,225 A | 7/2000 | Winslow et al. |
| 6,083,228 A | 7/2000 | Michelson |
| 6,096,038 A | 8/2000 | Michelson |
| 6,102,949 A | 8/2000 | Biedermann et al. |
| 6,102,950 A | 8/2000 | Vaccaro |
| 6,113,638 A | 9/2000 | Williams et al. |
| 6,113,639 A | 9/2000 | Ray et al. |
| 6,123,705 A | 9/2000 | Michelson |
| 6,126,689 A | 10/2000 | Brett |
| 6,136,031 A | 10/2000 | Middleton |
| 6,156,037 A | 12/2000 | LeHuec et al. |
| 6,159,211 A | 12/2000 | Boriani et al. |
| 6,159,215 A | 12/2000 | Urbahns et al. |
| 6,159,244 A | 12/2000 | Suddaby |
| 6,159,245 A | 12/2000 | Meriwether et al. |
| 6,174,334 B1 | 1/2001 | Suddaby |
| 6,179,873 B1 | 1/2001 | Zientek |
| 6,183,517 B1 | 2/2001 | Suddaby |
| 6,193,755 B1 | 2/2001 | Metz-Stevenhagen et al. |
| 6,193,757 B1 | 2/2001 | Foley et al. |
| 6,200,348 B1 | 3/2001 | Biedermann et al. |
| 6,206,922 B1 | 3/2001 | Zdeblick et al. |
| 6,224,599 B1 | 5/2001 | Baynham et al. |
| 6,224,607 B1 | 5/2001 | Michelson |
| 6,235,059 B1 | 5/2001 | Benezech et al. |
| 6,245,108 B1 | 6/2001 | Biscup |
| 6,251,140 B1 | 6/2001 | Marino et al. |
| 6,261,296 B1 | 7/2001 | Aebi et al. |
| 6,267,763 B1 | 7/2001 | Castro |
| 6,270,498 B1 | 8/2001 | Michelson |
| 6,277,122 B1 | 8/2001 | McGahan et al. |
| 6,283,966 B1 | 9/2001 | Houfburg |
| 6,290,724 B1 | 9/2001 | Marino |
| 6,302,914 B1 | 10/2001 | Michelson |
| 6,319,257 B1 | 11/2001 | Carignan et al. |
| 6,332,887 B1 | 12/2001 | Knox |
| 6,332,895 B1 | 12/2001 | Suddaby |
| 6,364,880 B1 | 4/2002 | Michelson |
| 6,371,987 B1 | 4/2002 | Weiland et al. |
| 6,409,766 B1 | 6/2002 | Brett |
| 6,419,705 B1 | 7/2002 | Erickson |
| 6,423,095 B1 | 7/2002 | Van Hoeck et al. |
| 6,428,541 B1 | 8/2002 | Boyd et al. |
| 6,428,544 B1 | 8/2002 | Ralph et al. |
| 6,432,106 B1 | 8/2002 | Fraser |
| 6,436,098 B1 | 8/2002 | Michelson |
| 6,436,101 B1 | 8/2002 | Hamada |
| 6,447,512 B1 | 9/2002 | Landry et al. |
| 6,447,544 B1 | 9/2002 | Michelson |
| 6,454,805 B1 | 9/2002 | Baccelli et al. |
| 6,454,806 B1 | 9/2002 | Cohen et al. |
| 6,458,159 B1 | 10/2002 | Thalgott |
| 6,468,311 B2 | 10/2002 | Boyd et al. |
| 6,478,800 B1 | 11/2002 | Fraser et al. |
| 6,478,801 B1 | 11/2002 | Ralph et al. |
| 6,478,823 B1 | 11/2002 | Michelson |
| 6,482,233 B1 | 11/2002 | Aebi et al. |
| 6,488,710 B2 | 12/2002 | Besselink |
| 6,491,724 B1 | 12/2002 | Ferree |
| 6,500,180 B1 | 12/2002 | Foley et al. |
| 6,517,544 B1 | 2/2003 | Michelson |
| 6,527,803 B1 | 3/2003 | Crozet et al. |
| 6,537,279 B1 | 3/2003 | Michelson |
| 6,551,316 B1 | 4/2003 | Rinner et al. |
| 6,562,074 B2 | 5/2003 | Gerbec et al. |
| 6,565,574 B2 | 5/2003 | Michelson |
| 6,569,168 B2 | 5/2003 | Lin |
| 6,582,431 B1 | 6/2003 | Ray |
| 6,585,749 B2 | 7/2003 | Hanson |
| 6,589,247 B2 | 7/2003 | McGahan et al. |
| 6,599,291 B1 | 7/2003 | Foley et al. |
| 6,599,292 B1 | 7/2003 | Ray |
| 6,607,559 B2 | 8/2003 | Ralph et al. |
| 6,635,086 B2 | 10/2003 | Lin |
| 6,641,582 B1 | 11/2003 | Hanson et al. |
| 6,641,614 B1 | 11/2003 | Wagner et al. |
| 6,648,917 B2 | 11/2003 | Gerbec et al. |
| 6,652,533 B2 | 11/2003 | O'Neil |
| 6,666,866 B2 | 12/2003 | Martz et al. |
| 6,676,703 B2 | 1/2004 | Biscup |
| 6,706,070 B1 | 3/2004 | Wagner et al. |
| 6,712,819 B2 | 3/2004 | Zucherman et al. |
| 6,712,825 B2 | 3/2004 | Aebi et al. |
| 6,719,796 B2 | 4/2004 | Cohen et al. |
| 6,730,126 B2 | 5/2004 | Boehm, Jr. et al. |
| 6,740,088 B1 | 5/2004 | Kozak et al. |
| 6,743,255 B2 | 6/2004 | Ferree |
| 6,746,450 B1 | 6/2004 | Wall et al. |
| 6,746,454 B2 | 6/2004 | Winterbottom et al. |
| 6,749,635 B1 | 6/2004 | Bryan |
| 6,755,841 B2 | 6/2004 | Fraser et al. |
| 6,758,849 B1 | 7/2004 | Michelson |
| 6,767,367 B1 | 7/2004 | Michelson |
| 6,770,074 B2 | 8/2004 | Michelson |
| 6,770,096 B2 | 8/2004 | Bolger et al. |
| 6,793,658 B2 | 9/2004 | LeHuec et al. |
| 6,824,565 B2 | 11/2004 | Muhanna et al. |
| 6,827,740 B1 | 12/2004 | Michelson |
| 6,830,589 B2 | 12/2004 | Erickson |
| 6,840,941 B2 | 1/2005 | Rogers et al. |
| 6,852,129 B2 | 2/2005 | Gerbec et al. |
| 6,855,148 B2 | 2/2005 | Foley et al. |
| 6,863,673 B2 | 3/2005 | Gerbec et al. |
| 6,875,213 B2 | 4/2005 | Michelson |
| 6,884,242 B2 | 4/2005 | LeHuec et al. |
| 6,893,464 B2 | 5/2005 | Kiester |
| 6,902,566 B2 | 6/2005 | Zucherman et al. |
| 6,923,830 B2 | 8/2005 | Michelson |
| 6,929,647 B2 | 8/2005 | Cohen |
| 6,955,691 B2 | 10/2005 | Chae et al. |
| 6,966,912 B2 | 11/2005 | Michelson |
| 6,974,480 B2 | 12/2005 | Messerli et al. |
| 6,976,988 B2 | 12/2005 | Ralph et al. |
| 6,981,975 B2 | 1/2006 | Michelson |

| | | |
|---|---|---|
| 6,986,772 B2 | 1/2006 | Michelson |
| 7,004,947 B2 | 2/2006 | Shluzas |
| 7,018,415 B1 | 3/2006 | McKay |
| 7,018,416 B2 | 3/2006 | Hanson et al. |
| 7,033,394 B2 | 4/2006 | Michelson |
| 7,041,135 B2 | 5/2006 | Michelson |
| 7,051,417 B2 | 5/2006 | Michelson |
| 7,060,073 B2 | 6/2006 | Frey et al. |
| 7,066,961 B2 | 6/2006 | Michelson |
| 7,070,598 B2 | 7/2006 | Lim et al. |
| 7,077,864 B2 | 7/2006 | Byrd, III et al. |
| 7,081,118 B2 | 7/2006 | Weber |
| 7,083,650 B2 | 8/2006 | Moskowitz et al. |
| 7,087,055 B2 | 8/2006 | Lim et al. |
| 7,094,257 B2 | 8/2006 | Mujwid et al. |
| 7,108,698 B2 | 9/2006 | Robbins |
| 7,112,206 B2 | 9/2006 | Michelson |
| 7,112,224 B2 | 9/2006 | Liu |
| 7,115,132 B2 | 10/2006 | Errico |
| 7,115,143 B1 | 10/2006 | Michelson |
| 7,118,579 B2 | 10/2006 | Michelson |
| 7,135,043 B2 | 11/2006 | Nakahara et al. |
| 7,137,997 B2 | 11/2006 | Paul |
| 7,144,275 B2 | 12/2006 | Iida |
| 7,153,303 B2 | 12/2006 | Squires |
| 7,153,304 B2 | 12/2006 | Robie et al. |
| 7,160,304 B2 | 1/2007 | Michelson |
| 7,163,561 B2 | 1/2007 | Michelson |
| 7,166,129 B2 | 1/2007 | Michelson |
| 7,166,130 B2 | 1/2007 | Ferree |
| 7,169,152 B2 | 1/2007 | Foley |
| 7,169,153 B2 | 1/2007 | Keller |
| 7,169,182 B2 | 1/2007 | Errico et al. |
| 7,172,627 B2 | 2/2007 | Fiere et al. |
| 7,189,242 B2 | 3/2007 | Boyd et al. |
| 7,189,244 B2 | 3/2007 | Newton |
| 7,207,991 B2 | 4/2007 | Michelson |
| 7,211,085 B2 | 5/2007 | Michelson |
| 7,211,100 B2 | 5/2007 | Hanson |
| 7,217,292 B2 | 5/2007 | Ralph et al. |
| 7,217,293 B2 | 5/2007 | Branch, Jr. |
| 7,229,477 B2 | 6/2007 | Biscup |
| 7,232,463 B2 | 6/2007 | Falahee |
| 7,235,081 B2 | 6/2007 | Errico et al. |
| 7,235,082 B2 | 6/2007 | Bartish |
| 7,244,275 B2 | 7/2007 | Michelson |
| 7,255,698 B2 | 8/2007 | Michelson |
| 7,288,093 B2 | 10/2007 | Michelson |
| 7,288,095 B2 | 10/2007 | Baynham et al. |
| 7,303,565 B2 | 12/2007 | Buttermann |
| 7,594,932 B2 | 9/2009 | Aferzon |
| 7,727,280 B2 | 6/2010 | McLuen |
| 8,070,819 B2 | 12/2011 | Aferzon |
| 8,100,972 B1 | 1/2012 | Bruffey et al. |
| 8,142,508 B1 | 3/2012 | Bruffey et al. |
| 8,147,521 B1 | 4/2012 | Cornwall et al. |
| 8,167,950 B2 | 5/2012 | Aferzon et al. |
| 2002/0128713 A1 | 9/2002 | Ferree |
| 2003/0023312 A1 | 1/2003 | Thalgott |
| 2003/0040798 A1 | 2/2003 | Michelson |
| 2004/0117020 A1 | 6/2004 | Frey et al. |
| 2004/0153156 A1 | 8/2004 | Cohen |
| 2004/0215198 A1 | 10/2004 | Marnay |
| 2005/0021041 A1 | 1/2005 | Michelson |
| 2005/0080422 A1 | 4/2005 | Otte |
| 2005/0087628 A1 | 4/2005 | Sayar |
| 2005/0107878 A1 | 5/2005 | Conchy |
| 2005/0187628 A1 | 8/2005 | Michelson |
| 2005/0216083 A1 | 9/2005 | Michelson |
| 2005/0283236 A1 | 12/2005 | Razian |
| 2006/0036247 A1 | 2/2006 | Michelson |
| 2006/0058793 A1 | 3/2006 | Michelson |
| 2006/0058876 A1 | 3/2006 | McKinley |
| 2006/0058878 A1 | 3/2006 | Michelson |
| 2006/0069442 A1 | 3/2006 | Michelson |
| 2006/0079962 A1 | 4/2006 | Michelson |
| 2006/0085001 A1 | 4/2006 | Michelson |
| 2006/0100633 A1 | 5/2006 | Michelson |
| 2006/0106395 A1 | 5/2006 | Link |
| 2006/0116768 A1 | 6/2006 | Krueger et al. |
| 2006/0122701 A1 | 6/2006 | Kiester |
| 2006/0142859 A1 | 6/2006 | McLuen |
| 2006/0200138 A1 | 9/2006 | Michelson |
| 2006/0200164 A1 | 9/2006 | Michelson |
| 2006/0206207 A1 | 9/2006 | Dryer et al. |
| 2006/0241764 A1 | 10/2006 | Michelson |
| 2006/0265077 A1 | 11/2006 | Zwirkoski |
| 2007/0032871 A1 | 2/2007 | Michelson |
| 2007/0055376 A1 | 3/2007 | Michelson |
| 2007/0100452 A1 | 5/2007 | Prosser |
| 2007/0276370 A1 | 11/2007 | Altarac |
| 2007/0288007 A1 | 12/2007 | Burkus et al. |
| 2007/0293949 A1 | 12/2007 | Salerni |
| 2008/0027550 A1 | 1/2008 | Link et al. |
| 2008/0103501 A1 | 5/2008 | Ralph et al. |
| 2008/0132949 A1 | 6/2008 | Aferzon et al. |
| 2009/0365007 | 10/2009 | Colleran |
| 2010/0030334 A1 | 2/2010 | Molz, IV |
| 2010/0305704 A1 | 12/2010 | Messerli et al. |

FOREIGN PATENT DOCUMENTS

| | | |
|---|---|---|
| EP | 1374809 | 1/2004 |
| FR | 2880795 | 1/2005 |
| JP | 2010051651 | 3/2010 |
| WO | WO-2010037926 | 4/2010 |

LONGITUDINAL
DIRECTION

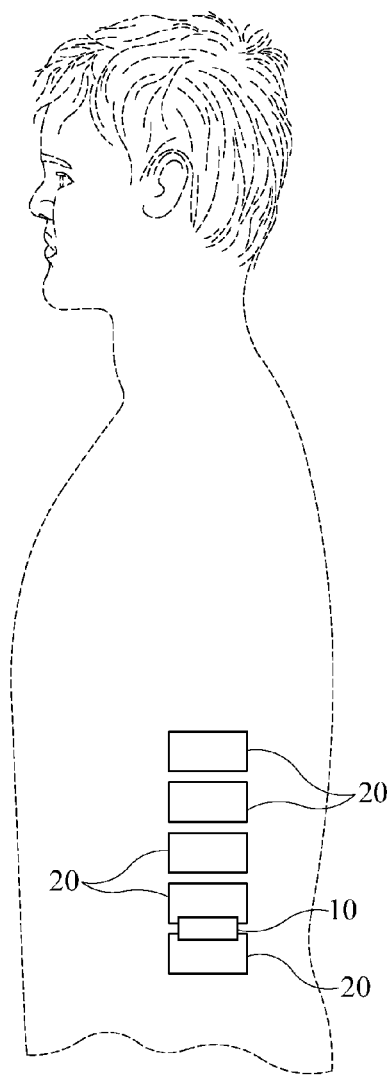
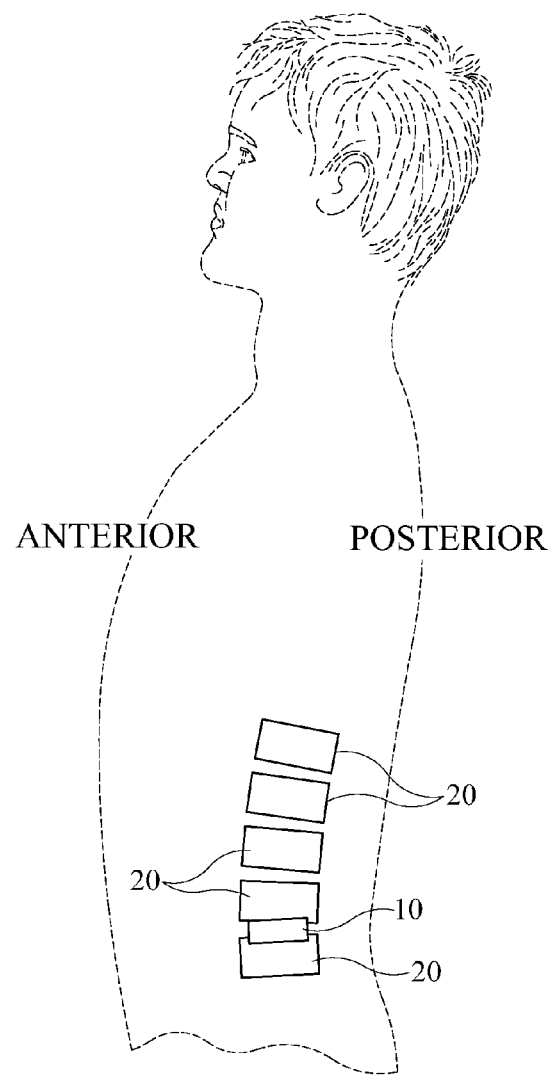
FIG. 2A
PRIOR ART
FIG. 2B
PRIOR ART

DEPLOYABLE MEMBER FOR USE WITH AN INTERVERTEBRAL CAGE

CROSS-REFERENCE TO RELATED APPLICATIONS

This application claims priority and benefit under 35 U.S.C. §119(e) to U.S. Provisional App. No. 61/165,267, filed on Mar. 31, 2009. This application is a continuation-in-part of and claims priority and benefit under 35 U.S.C. §120 to U.S. patent application Ser. Nos. 12/409,435, now abandoned and 12/409,410, now abandoned each filed on Mar. 23, 2009 and each of which is a continuation-in-part of and claims priority and benefit under 35U.S.C. §120 to U.S. patent application Ser. No. 12/167,218, filed on Jul. 2, 2008, now U.S. Pat. No. 8,142,508 which claims priority and benefit under 35 U.S.C. §119(e) to the following U.S. Provisional App. Nos. 61/037,551, filed on Mar. 18, 2008; 61/027,260, filed on Feb. 8, 2008; and 60/947,557, filed on Jul. 2, 2007. This application is also a continuation-in-part of and claims priority and benefit under 35 U.S.C. §120 to U.S. patent application Ser. No. 12/368,898, filed on Feb. 10, 2009, now U.S. Pat. No. 8,292,958 which is a continuation-in-part of and claims priority and benefit under 35 U.S.C. §120 to copending U.S. patent application Ser. No. 12/167,218, filed on Jul. 2, 2008, which claims priority and benefit under 35 U.S.C. §119(e) to the following U.S. Provisional App. Nos. 61/037,551, filed on Mar. 18, 2008; 61/027,260, filed on Feb. 8, 2008; and 60/947,557, filed on Jul. 2, 2007. This application is also a continuation-in-part of and claims priority and benefit under 35 U.S.C. §120 to the following U.S. patent application Nos. 12/368,895 now abandoned; 12/368,893 now abandoned; 12/368,890 now U.S. Pat. No. 8,366,774; and 12/368,888 now U.S. Pat. No. 8,100,972, each filed on Feb. 10, 2009 and each of which is a continuation of and claims priority and benefit under 35U.S.C. §120 to copending U.S. patent application Ser. No. 12/167,218, filed on Jul. 2, 2008, which claims priority and benefit under 35 U.S.C. §119(e) to the following U.S. Provisional App. Nos. 61/037,551, filed on Mar. 18, 2008; 61/027,260, filed on Feb. 8, 2008; and 60/947,557, filed on Jul. 2, 2007. This application is also a continuation-in-part of and claims priority and benefit under 35 U.S.C. §120 to copending U.S. patent application Ser. No. 12/167,218, filed on Jul. 2, 2008, which claims priority and benefit under 35 U.S.C. §119(e) to the following U.S. Provisional App. Nos. 61/037,551, filed on Mar. 18, 2008; 61/027,260, filed on Feb. 8, 2008; and 60/947,557, filed on Jul. 2, 2007. The entire contents of the aforementioned applications are herein incorporated by reference.

TECHNICAL FIELD

This invention pertains to surgery involving the spine.

BACKGROUND

Some interbody spacers for spinal fusion are intended to engage the bone of adjacent vertebrae so that the implant does not become dislodged when the patient moves. A particular form of patient motion which may be considered in lumbar fusion patients is extension, which is exhibited when a patient bends backwards.

SUMMARY

Embodiments disclosed herein may include an assembly of a spinal cage and a spin-plate in which the spin-plate blade may have an approximately flat side surface.

In one embodiment, the blade may have a groove recessed into the side surface, with the groove penetrating deeper into the side surface than a remainder of the side surface.

In another embodiment, the blade may possess an overhang extending from the side surface at least partially along a direction of the rotational axis of the spin-plate.

In other embodiments, the shape of an overhang or groove may be such as to draw vertebral bone toward the spinal cage as the spin-plate advances in its intended direction of rotation for deployment.

In yet another embodiment, a blade may have a blade cross-section that is taken in a cross-sectional plane that includes the rotational axis and intersects the blade, and, in that blade cross-section, a more radially-outward portion of the blade cross-section may have a greater dimension along the direction of the rotational axis than does a more radially-inward portion of the blade cross-section.

Another embodiment may be provided with a body and a spin-plate having a blade, and further may have at least one pin implantable in an adjacent vertebra, wherein a leading edge of the blade may have a slot or a hook shape having a hook shape interior, such that, when the spin-plate is in a deployed position, the first pin is located within the hook shape interior.

The grooves or overhangs described herein may be suitable to engage bone.

Other embodiments may provide surgical methods involving the use of the described embodiments.

BRIEF DESCRIPTION OF THE ILLUSTRATIONS

Embodiments of the invention are further described in the following illustrations.

FIG. 1 is a perspective view of an intervertebral implant in place in a patient's spine.

FIG. 2A schematically shows a patient's spine, containing an implant, with the patient's spine in a straight position.

FIG. 2B shows the patient's spine when such a patient is bending in extension.

DETAILED DESCRIPTION

In particular embodiments, there is provided an implant having a spinal cage and a spin-plate.

Figure 1:
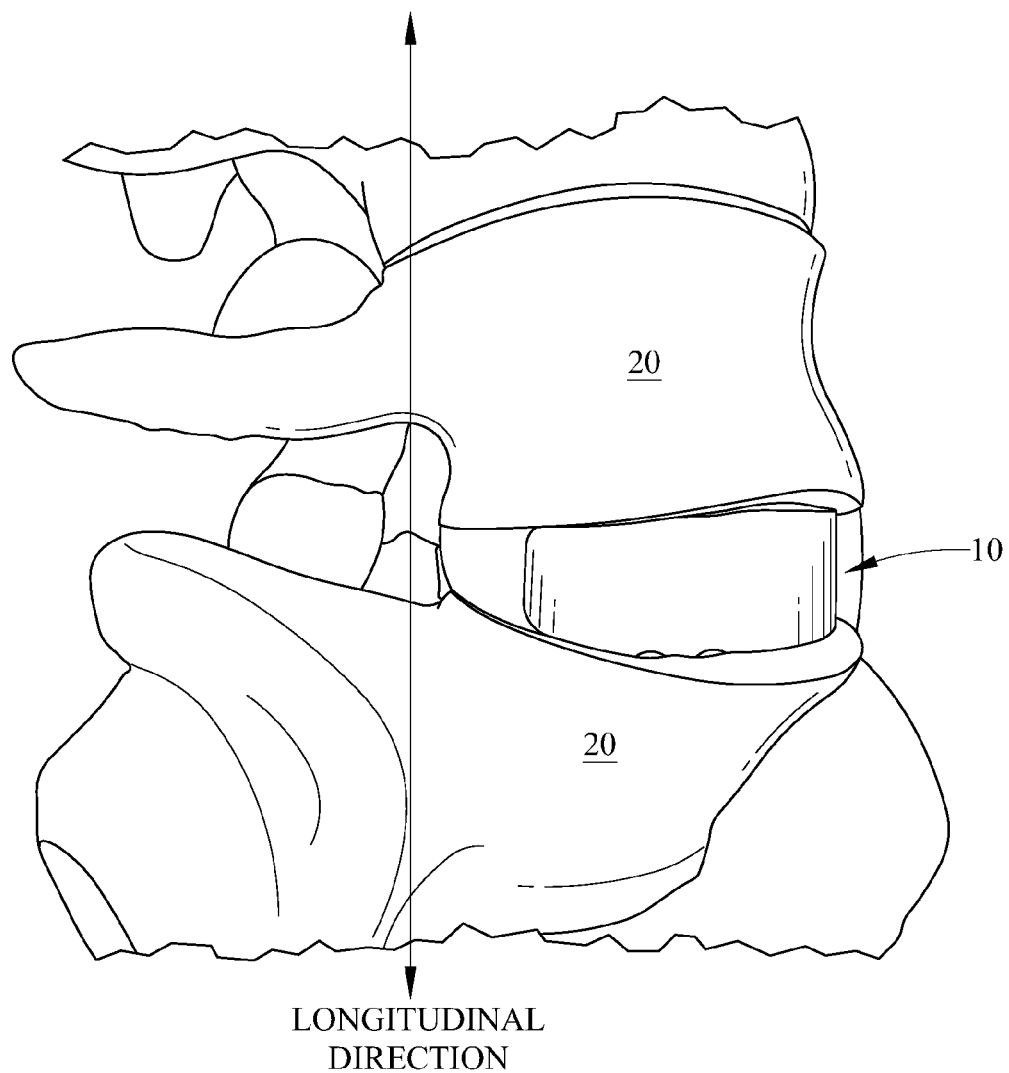

FIG. 1 illustrates a typical interbody device 10 implanted in a patient's spine between adjacent vertebrae 20. FIG. 2A schematically shows a patient's spine, containing a typical interbody device 10 implanted between adjacent vertebrae 20, with the patient's spine in a straight position. FIG. 2B shows such a patient bending in extension. In the situation of FIG. 2B, there is the possibility that the interbody device 10 may become dislodged and may move anteriorly. This illustration is especially pertinent to devices that have been implanted from an anterior approach, such as for Anterior Lumbar Interbody Fusion.

Figure 3:
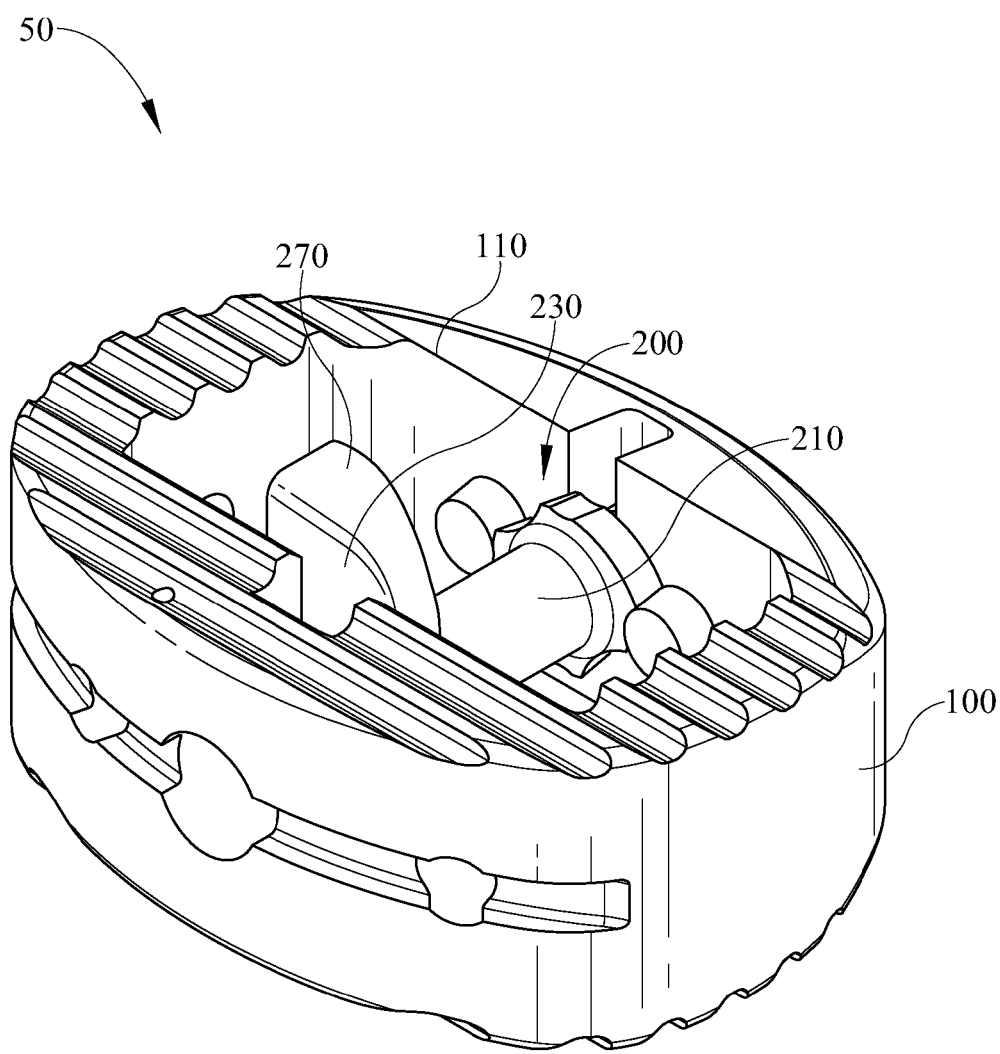
FIG. 3 is a perspective view of an intervertebral implant comprising a spinal cage containing a spin-plate.

FIG. 3 illustrates an embodiment of an implant 50 provided with a body 100 and a spin-plate 200. The body 100 may be a spinal cage and may be dimensioned to fit between adjacent vertebrae 20 (not shown). The body 100 may have empty space in its interior 110. The spin-plate 200 may be assembled or capable of being assembled to body 100 and may be rotatable with respect thereto. The spin-plate 200 may be removable from body 100 such as for ease of sterilization or replacement, or, alternatively, the spin-plate 200 may be permanently connected to or trapped in the body 100. The spin-plate 200 may be rotatable between an undeployed position and a deployed position. The rotational angle interval between the undeployed and deployed positions may be approximately 90 degrees. Alternatively, the rotational angle interval may be less than 90 degrees.

As illustrated in FIGS. 3-6B, the spin-plate 200 may be provided with a shaft 210 and a spin-plate blade 230. The spin-plate blade 230 may be integral with shaft 210 or may be attached to the shaft 210. The shaft 210 and the spin-plate 200 in general may be rotatable around a rotational axis 201. The blade 230 is illustrated as substantially lying in a blade plane that is perpendicular to rotational axis 201, although other orientations of the blade 230 are also possible. The blade 230 may have a flat surface that may substantially lie in a plane that is perpendicular to rotational axis 201.

With reference to FIGS. 4-6B, for use in describing the spin-plate 200, a spin-plate 200 may have an intended direction of rotation from an undeployed position to a deployed position. There may be designated leading edges 236 and trailing edges 238 of spin-plate blade 230. When the spin-plate is rotated in the intended direction, a leading edge 236 may meet oncoming bone (not shown). A trailing edge 238 may follow the leading edge 236 with respect to its intended direction of rotation for deployment. The leading edge 236 and the trailing edge 238 may be considered to be located in alternating quadrants (angular intervals of approximately 90 degrees), with the angular measurement being centered at the axis of rotation 201 of the spin-plate 200. The leading edge 236 of the spin-plate blade 230 may be of different geometry from the geometry of the trailing edge 238 of the spin-plate blade 230. It is possible that the leading edge 236 of the spin-plate blade 230 might be tapered in any one direction or more than one direction. The same may be true for an overhang if present. A leading edge or cutting surface 236 of spin-plate blade 230 may possess a material that is harder than the hardness of some other parts of spin-plate blade 230 or spin-plate 200, for example the leading edge may possess a coating or inserts, or may undergo special treatment which may be different from treatment of the remainder of the blade 230.

The blade 230 may have a cross-section (cross-section being taken in a cutting plane that includes the axis of rotation 201 of the spin-plate) such that a more radially-outward portion of the blade is wider than a more radially-inward portion of the blade. The blade 230 illustrated in FIGS. 3-6B has such a property because the overhang 270 has a longer dimension along the direction of the rotational axis 201 than a remainder of the blade 230. Alternatively, a similar geometry may be achieved with a more gradual variation in the thickness (measured in a direction along axis of rotation 201) of blade 230.

Figure 4:
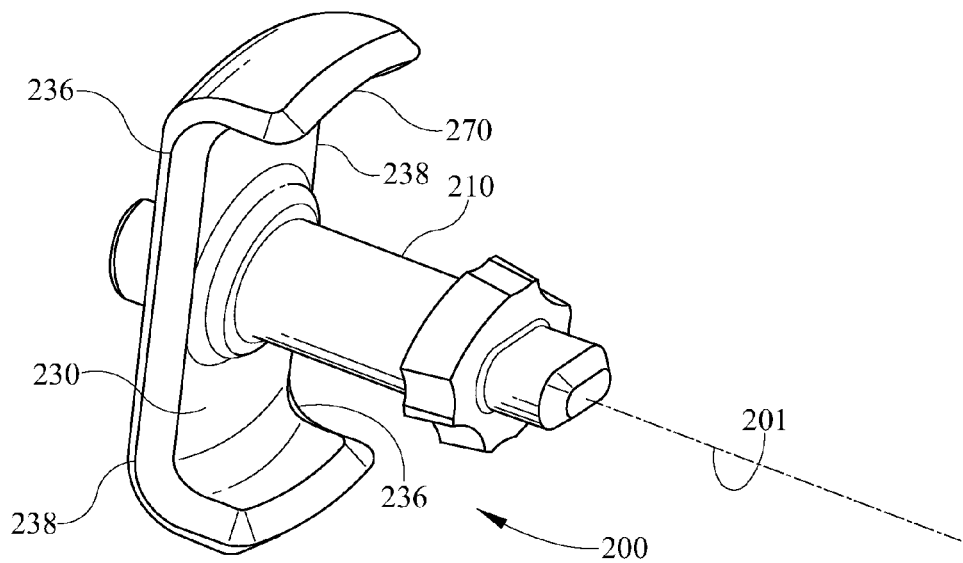
FIG. 4 is a perspective view of a spin-plate having an overhang that has a configuration that may be termed a circumferential configuration.

Referring now to FIG. 4, the outline of the blade 230 (when viewed along the rotational axis 201) is partly rectangular and partly rounded. In this illustration, the overhang 270 approximately follows the contour of an outer portion of the blade 230. Some of the contour of the blade 230 (when viewed along the axis of rotation 201) has portions of circular arcs whose center is the rotational axis 201. As illustrated, the overhang 270 is of approximately constant thickness in a radial direction (with respect to rotational axis 201), except for a slight taper in the immediate vicinity of the leading edge. In this situation, the overhang 270 would follow in its own path in the vertebral bone, as the spin-plate 200 rotates to advance from an undeployed position to a deployed position. This may be described as the overhang 270 having a purely circumferential geometry with respect to the rotational axis 201. As illustrated, the overhang 270 exists only near the outer edge of blade 230.

Figure 5:
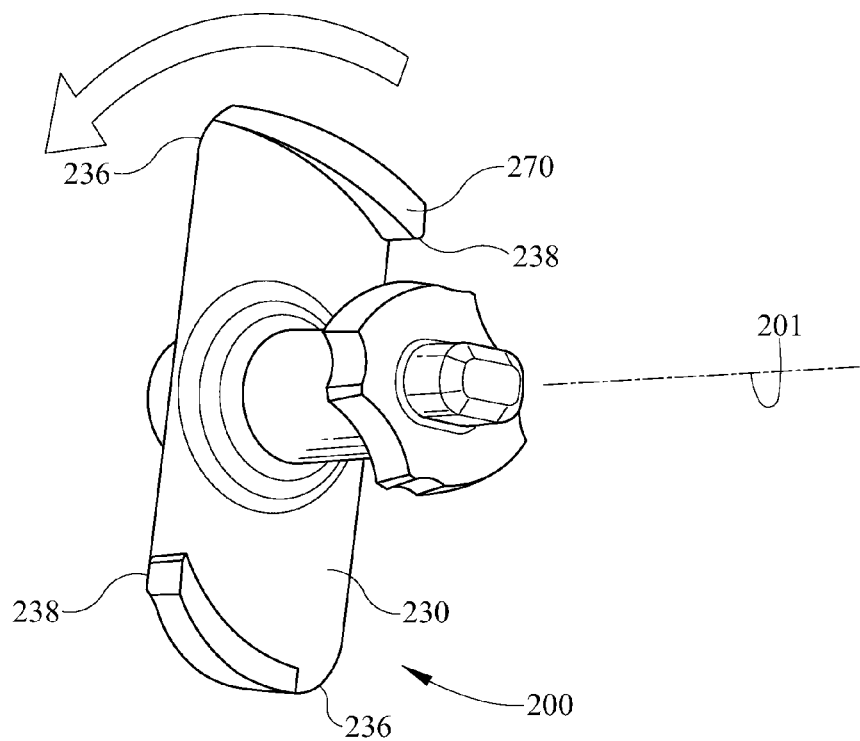
FIG. 5 is a perspective view of a spin-plate having an overhang that has a configuration that tends to draw vertebral bone towards a central body as rotational deployment of the spin-plate advances.

Referring to FIG. 5, at least one surface of the overhang 270, such as the surface facing towards rotational axis 201, is not a circular arc centered at rotational axis 201. The curvature of the overhang surface facing towards rotational axis 201 may be such that as the spin-plate 230 advances rotationally during deployment, the overhang 270 may exert force pulling vertebral bone toward the implant body 100. The thickness of the overhang 270 (in the radial direction with respect to rotational axis 201) has been illustrated as being variable as a function of angular position, but of course it would also be possible for that thickness to be constant.

Figures 6A, 6B:
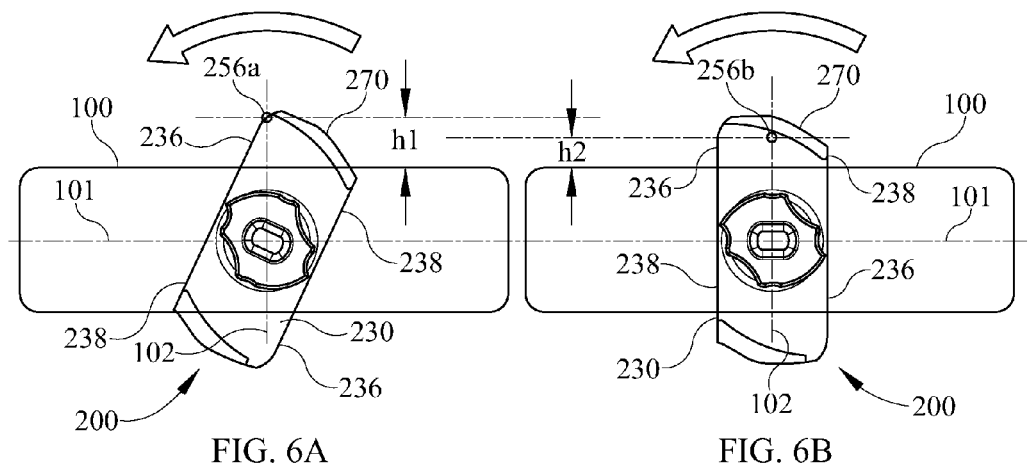
FIG. 6A is an end view of a spin-plate of FIG. 5 in a partially-deployed position.
FIG. 6B is an end view of a spin-plate of FIG. 5 in a fully-deployed position.

Use of the spin-plate of FIG. 5 is further illustrated in FIGS. 6A and 6B, which illustrate different points during the rotation and deployment of spin-plate 200. For ease of illustration, FIGS. 6A and 6B are shown side-by-side with the horizontal mid-planes 101, 102 of body 100 aligned with each other. To help in such visualization, one may visualize a point 256a, 256b in vertebral bone, located directly above the axis of rotation of spin-plate 200, that interacts with the implant-facing edge of the overhang 270. FIG. 6A illustrates the situation where the advancing tip of the overhang 270 just begins to meet the vertical axis of the spine or of the implant. In this situation, the point of vertebral bone that is in contact with the implant-facing surface of overhang 270 is illustrated as point 256a. FIG. 6B illustrates the situation where the spin-plate is in its fully-deployed position and the blade of spin-plate 200 is generally vertically oriented. In this situation, the point of vertebral bone that is in contact with the implant-facing surface of the overhang 270 is illustrated as point 256b.

As can be seen, point 256b is closer to the implant body 100 than is point 256a. This difference between the vertical position of point 256b and the vertical position of point 256a represents an amount by which bone can be pulled together by the rotating of spin-plate 200. An amount of pulling-together could be either greater or lesser than illustrated, depending on the shape of the overhang 270. If the vertebra does not actually move in response to rotational advancement of blade 230 and overhang 270, it is still possible that such rotational advancement of the type illustrated here could generate local deformation of vertebral bone which maintains the vertebral bone in tight contact relation with the implant body 100 or increases the contact force of vertebral bone against implant body 100.

Although FIGS. 3-6B have illustrated an overhang 270 on one particular side of blade 230, it is further possible that an overhang 270 could be provided on either side of blade 230, or on both of the two opposed sides of blade 230. It is further possible that more than one overhang 270 might be provided on any given side of a blade 230. Although overhangs 270 have been illustrated as being continuous along the relevant portions of the blade 230, it is also possible that an overhang 270 could be interrupted. The overhang 270 may have, at its leading edge, a point or taper in any desired direction. The thickness of blade 230, along the direction of rotational axis 201, has been illustrated as being constant, but could be variable if desired.

Figure 7A:
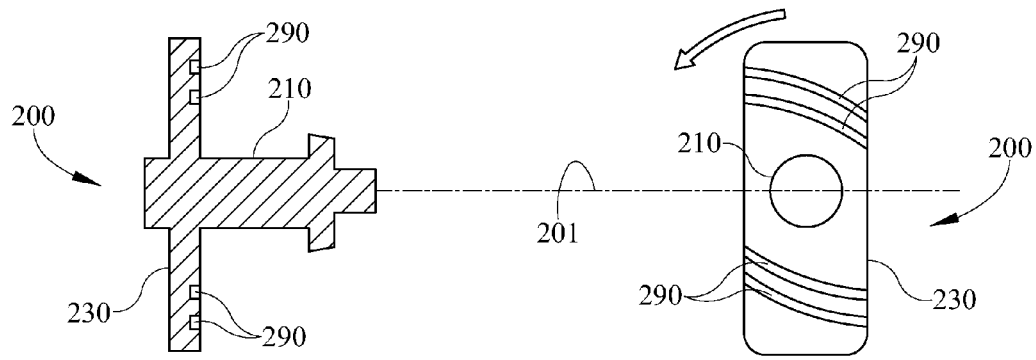
FIG. 7A is a sectional view of a spin-plate blade that has simple grooves in a side surface.
Figure 7B:
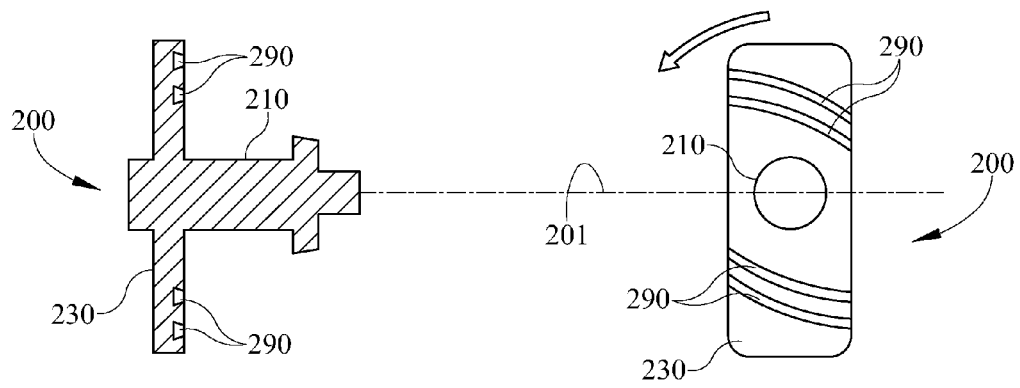
FIG. 7B is a sectional view of a spin-plate blade that has undercut grooves in a side surface.

Referring now to FIGS. 7A and 7B, there may be provided a blade 230 that might not contain a distinct identifiable overhang 270 protruding from a mostly flat side surface of the blade, as has been illustrated in FIG. 4-6B, but rather the blade 230 might have a generally flat side surface into which are recessed one or more grooves 290. Grooves 290 are intended to cut into bone tissue, or allow space for bone in-growth, or both. Such grooves 290 might, in cross-section, be simple rectangular grooves as illustrated in FIG. 7A, or could comprise an undercut as is illustrated in FIG. 7B. For example, an undercut groove could have a trapezoidal cross-section. A trapezoidal shape may comprise a shorter base dimension and a longer base dimension parallel to the shorter base dimension. In this situation, the dimension of the trapezoid at the surface of the blade 230 may be the smaller base dimension and the dimension of the trapezoid recessed in the interior of the blade 230 may be the longer base dimension of the trapezoid. Any other desired groove cross-section could also be provided. For example, a trapezoidal shaped groove would be undercut at both sides of the groove, but undercutting on only one side is also possible. Groove cross-sectional shapes including curved segments are also possible. Of course, such grooves 290 could be provided on one side of blade 230 as illustrated in FIGS. 7A and 7B, or on the opposite side of blade 230, or on both sides of blade 230. Along the direction of rotation of the blade 230, the groove 290 could follow a path that is purely circumferential, which would be analogous to the circumferential variety of overhang 270 illustrated elsewhere herein, or could follow any other desired path. For example, if the path of the groove becomes more radially inward as one goes from the leading edge 236 of the blade 230 towards the trailing edge 238, this could produce an action tending to pull vertebrae towards each other, as described elsewhere herein in connection with overhangs. Grooves 290 have been illustrated as being of constant width and depth along the direction from leading edge to trailing edge, but either width or depth could be variable.

Figure 8:
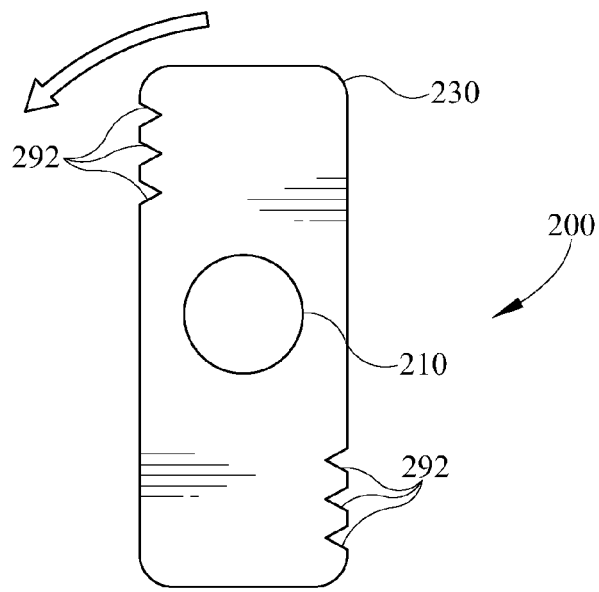
FIG. 8 shows a spin-plate having teeth on its leading edge.

FIG. 8 illustrates a spin-plate blade having teeth 292 in the leading edge of the blade 230.

Figure 9:
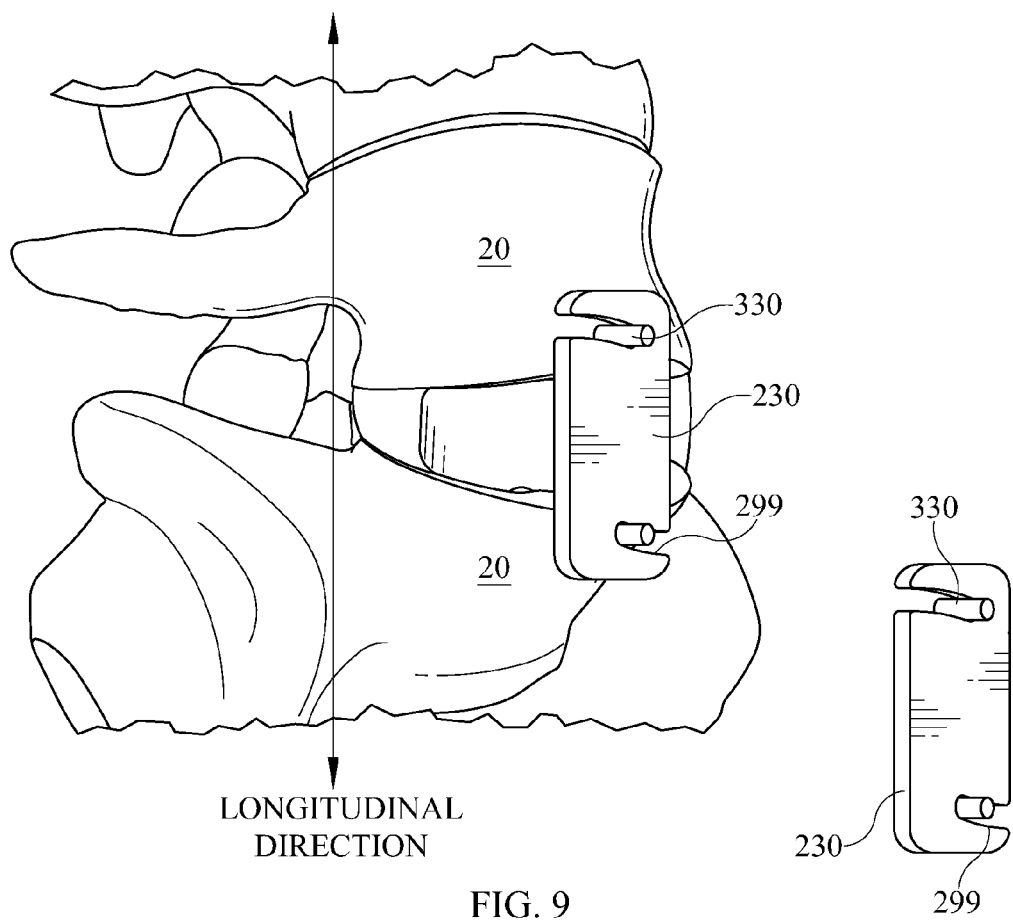
FIG. 9 shows a spin-plate having a slot capable of engaging a rod embedded in a vertebra.

Yet another embodiment is illustrated in FIG. 9. It is possible that blade 230 could have a slot 299 therethrough starting along a leading edge of blade 230 with respect to the direction of rotational advancement of blade 230 during deployment, and proceeding partway along the blade 230. This could be described as creating a hook shape. Such a blade 230 may be used in conjunction with a pin 330 that may be disposed in the vertebra 20. When blade 230 is in its deployed position, pin 330 may be disposed in the interior of the hook shape. When blade 230 is in its deployed position, pin 330 may interact with the hook shape of blade 230, although that is not essential. The path of slot 299 as a function of rotational position of spin-plate 200 may be such that as deployment advances, the blade 230 interacts with pin 330 to draw the vertebra 20 closer to body 100, or causes exertion of greater contact force by vertebra 20 on body 100. This may be an action similar to that displayed by the overhang 270 as illustrated in FIG. 5 and FIGS. 6A and 6B. A pin 330 may be used in both of the adjacent vertebrae 20. Although, if desired, the pin 330 might be used in only one of the vertebrae 20.

The body 100 may be made of a biocompatible metal or could be made of suitably strong biocompatible polymer. The spin-plate 200 also may be made of a biocompatible metal or other suitably strong material. If the spin-plate 200 and the body 100 are provided separately or are separable from each other, they may be provided in the form of a kit comprising various bodies 100 and various spin-plates 200. It is possible that at least some of bodies 100 and spin-plates 200 may be interchangeable such that more than one spin-plate 200 can fit within a certain body 100, or more than one body 100 may be matched with a given spin-plate 200, or both. Various spin-plates 200 in a kit may have different properties as far as overhangs 270, grooves 290, or hook shape or slot 299.

Further variations are possible from what has been described. For example, although a spin-plate 200 has been illustrated whose blade 230 has a pair of substantially identical cutting edges symmetrically located 180 degrees apart from each other, it is not necessary that the two ends of the blade 230 be exactly identical to each other. Opposite ends of the blade 230 might be different from each other in any desired respect, or it is even possible that one of them could be absent. The blade 230 could also have holes therethrough from one side surface to an opposed side surface of blade 230.

In general, the described overhangs 270 or grooves 290 or similar features could act to prevent sliding motion of the blade 230 with respect to neighboring vertebral bone material even if the patient performs a motion, for example, involving extension, that might (in the absence of a feature such as overhang 270 or groove 290) tend to cause separation between the vertebra and the body 100, or sliding of vertebral bone relative to the blade 230.

Embodiments of the invention may also provide a surgical method or methods. The method may provide implanting in a patient an implant comprising a body 100 and a spin-plate 200 assembled to the body 100 and rotatable with respect thereto, followed by rotating the spin-plate 200 from an undeployed position to a deployed position. The spin-plate 200 may have features as described elsewhere herein. The surgical method may further provide implanting a pin or pins 330 into vertebrae, in positions suitable for interaction with spin-plate 200 or suitable to be located within a hook region or a slot 299 of spin-plate 200 when spin-plate 200 is in its deployed position.

Features described herein may be combined in any combination. Steps of a method described herein may be performed in any sequence that is physically possible. Although the invention has been described herein, it is desired that the scope be limited only by the scope of the following claims.

The invention claimed is:

1. A spinal cage and spin-plate assembly, comprising:
   a spinal cage dimensioned to fit between adjacent vertebrae and having a central opening therethrough and having a cage flat inner surface along a portion of said central opening; and
   a spin-plate assembled to said spinal cage and rotatable with respect thereto, said spin-plate having a rotational axis, said spin-plate having a blade having a first side surface lying at least approximately in a spin-plate plane that is at least approximately perpendicular to said rotational axis and having a second side surface opposed to said first side surface, wherein said second side surface is adjacent to said cage flat inner surface, said spin-plate blade having a blade leading edge facing forward with respect to a direction of rotation about said rotational axis to deploy said spin-plate out of said spinal cage, at least a portion of said blade leading edge forming substantially a straight line, said blade leading edge having a taper in at least one direction, wherein said spin-plate further comprises an overhang at a radially outer region of said blade extending from said first side surface away from said cage flat inner surface at least partially along a direction of said rotational axis but not extending from said second side surface, wherein said overhang comprises a first surface and a second surface, wherein said first surface faces radially inward with respect to said rotational axis and said second surface faces radially outward, wherein said overhang comprises an overhang leading edge facing forward with respect to said direction of rotation about said rotational axis to deploy said spin-plate out of said spinal cage, and comprises an overhang trailing edge opposed to said overhang leading edge, wherein a first distance between said first surface and said axis of rotation measured at said leading edge is unequal to a second distance between said first surface and said axis of rotation measured at said trailing edge.

2. The spinal cage and spin-plate assembly of claim 1, wherein said overhang is located at an outer radial edge of said spin-plate.

3. The spinal cage and spin-plate assembly of claim 1, wherein a length of said overhang leading edge is equal to a length of said overhang trailing edge, as measured from said first side surface along said axis of rotation.

4. The spinal cage and spin-plate assembly of claim 1, wherein a length of said overhang leading edge is less than a length of said overhang trailing edge, as measured from said first side surface along said axis of rotation.

5. The spinal cage and spin-plate assembly of claim 1, wherein said overhang is tapered along one or more dimensions.

6. The spinal cage and spin-plate assembly of claim 1, wherein said overhang has a thickness in a radial direction with respect to said rotational axis, and said thickness varies continuously, being smaller near said overhang leading edge and larger near said overhang trailing edge.

* * * * *